United States Patent [19]

Spencer

[11] 4,003,255
[45] Jan. 18, 1977

[54] MEASUREMENT AND CONTROL OF FLUID FLOW

[75] Inventor: Jordan Spencer, Tenafly, N.J.

[73] Assignee: Robert I. Pearlman, Elizabeth, N.J.; a part interest

[22] Filed: Sept. 29, 1975

[21] Appl. No.: 617,600

Related U.S. Application Data

[63] Continuation-in-part of Ser. No. 467,264, May 7, 1974, abandoned.

[52] U.S. Cl. .................................. 73/194 E; 73/209; 73/453
[51] Int. Cl.$^2$ ............................................ G01F 1/28
[58] Field of Search ................. 73/194 E, 228, 453, 73/209

[56] References Cited
UNITED STATES PATENTS

| | | | |
|---|---|---|---|
| 2,775,126 | 12/1956 | Honick | 73/453 |
| 3,316,767 | 5/1967 | Leibert | 73/453 |
| 3,593,585 | 7/1971 | Bresson | 73/453 |
| 3,662,598 | 5/1972 | Spencer | 73/194 E |
| 3,847,020 | 11/1974 | Jurschak | 73/228 |

Primary Examiner—James J. Gill
Attorney, Agent, or Firm—Robert I. Pearlman

[57] ABSTRACT

An improved method and apparatus for measuring fluid flow and controlling fluid flow systems. The invention uses a magnetically responsive float normally resting in contact with a stop element positioned in the flow conduit, with magnetic means positioned upstream. The requisite increase of magnetic force to pull said float element from the stop element against the direction of fluid flow is related to the flow rate, thus serving to indicate same for metering or control purposes. Normally, the current to an electromagnet required to overcome the force of fluid flow is used as a measure of flow rate. This system can also be employed to determine fluid viscosity.

17 Claims, 4 Drawing Figures

MEASUREMENT AND CONTROL OF FLUID FLOW

CROSS REFERENCE TO RELATED APPLICATIONS

This application is a Continuation-in-Part of U.S. Ser. No. 467,264 filed for the present inventor on May 7, 1974, now abandoned.

BACKGROUND OF INVENTION

Control and measurement of flow of fluids, both gases and liquids, has presented considerable problems to the prior art, particularly at extremely low flow rates. Typically, prior art systems for use at low to moderate flow rates, e.g. rates of 1 $cm^3$/hr. to 1000 $cm^3$/hr. have proven to be either relatively inaccurate or fairly expensive in terms of having an accurate measuring system. Typical of known devices for this purpose are orifice or capillary meters connected to differential pressure transmitters, or, for larger flows, turbine meters.

The present invention teaches means for readily indicating flow rates of gases or liquids with a high degree of accuracy over a very wide range of flow rates by a relatively simple and inexpensive system. It can be automated to the point of adjusting flow conditions responsive to the measurement it obtains of fluid flow, and/or setting off suitable warning devices or the like when flow is above or below desired levels. The present system, which may use a glass or ceramic coated iron float in a quartz tube, can be used in very corrosive environments and/or at high temperatures. Due to its ability to inexpensively measure fluid flow at low flow rate, e.g. 5 $cm^3$/hr. to 1000 $cm^3$/hr., it offers the possibility of being used for intravenous flow control as described in U.S. Pat. No. 3,605,741, the general portions of which relating to intravenous flow being incorporated by reference herewith.

SUMMARY OF THE INVENTION

In accordance with the present invention, a float which normally may be in the form of a ball or the like and which is responsive to magnetic force rests against a stop element positioned in the conduit or flow tube by virtue of the movement of the fluid pressing the float against the stop. Upstream of the location of the stop element are positioned one or more magnetic means. Means are provided for controllably, i.e. slowly and gradually, increasing magnetic force of said magnetic means so as to attract said float away from the stop element due to the magnetic force and move it against the direction of fluid flow. Said means gradually increase the magnetic force continuously or stepwise until such time as its action on the magnetically responsive float overcomes the force of fluid flow and any gravitational forces. The requisite increase of magnetic force to said magnetic means to overcome the force of fluid flow is determined at the instant the float leaves the stop, and is related to the flow rate in the conduit thereby indicating the value of the flow rate.

Typically, the means for increasing the magnetic force exerted by said magnetic means may be means for gradually increasing current to an electromagnet, such as a current ramp generator or staircase generator (increases current in small, and preferably equal, discrete steps). The generator builds up the magnetic force of the magnetic means until the point at which the float is pulled back from the stop element. This point is detected by any of a variety of detection means responsive to the initial small change of position of the float element.

In a preferred aspect of the present invention, the detection means can be an optical system which sends off a beam of light passing across the tube or conduit in the area of said stop element and float resting against it. In this embodiment, the conduit in this area would be transparent and the float would serve to obscure the beam of light passing across the transparent tube, thereby preventing its impingement on a photodetector positioned on the opposite side of said tube. When the float is initially moved away from its rest position against the stop, the light beam is able to pass across the transparent tube and impinge upon the photodetector which in turn actuates the measurement of the current to the magnetic means, or other means for increasing the magnetic force required to cause said initial movement of the float element.

Alternative detectors can be used. By way of example, two plates of a capacitor can be positioned on either side of the normal resting point of the float element, and connected to an oscillator circuit. When the float element moves from its position between the plates it will change the capacitance of the capacitor, thus changing the frequency at which the oscillator operates and causing a sensing measurement to be taken of the relevant increase of magnetic force of said magnetic means to cause the float to move from its rest position. Alternative detection means include a strain gauge or piezoelectric sensor attached to the stop element, or means for passing a current through the float by contacts on the stop element, all of which would reflect movement of the float away from the stop element.

The float element, which preferably is the form of a ball, or right circular cylinder generally has a cross sectional area of about 50 to 95%, preferably 70 to 90%, of the conduit cross section in the area which it rests against the stopping element. It can be made of various materials so long as it is responsive to a magnetic field for moving it from its original position against the force of fluid flow. Thus, it can be a sphere of soft iron, a plastic or glass having a magnetically responsive material incorporated therein, e.g. iron or iron oxide powder, a ball of plated or unplated magnetic stainless steel, chrome plated soft iron or the like.

Floats designed to produce either laminar or turbulent flow conditions over a wide range of flows are also contemplated.

The conduit in the area containing said stop element may be the usual conduit through which the fluid flows or alternatively may be a special section utilized for flow measurement. In the latter case, it can be an especially tapered tube although normally a cylindrical tube is quite adequate. It can be mounted in any position, e.g. vertically, horizontally or at an angle. In cases when using a light source detector at least the area surrounding said stop element would be made of a transparent material, e.g. plastic, glass or fused quartz, so as to permit a light source detector to operate and detect the movement of the float element from its rest position against the stopping element.

The stopping element can be any means for halting the further flow of the magnetically responsive float without substantially impeding the flow of fluids through the conduit system. It can be made of plastic, glass, non-magnetic metal, wood, etc. The relative diameter of the conduit, float element, and stopping element should be related so that the float rests against the stop element in normal position without blocking passage of fluid flow through the conduit. By proper design of the stop element, the taper, if any, of the tube in the area of flow measurement, the pole pieces of the magnet and the shape and weight of the float or ball, the latter can be caused to leave its position against the stop element rapidly and cleanly with a "snap action" when the critical increase of magnetic force, e.g. critical current increase or current value, is reached for just overcoming the force of fluid flow. This gives a meter of high accuracy and sensitivity.

Normally, a pair of fixed electromagnets positioned upstream from said stop element is used together with means for increasing the current to said electromagnets so as to increase magnetic force and cause the float element to move away from its rest position. However, it is possible to alternatively increase the magnetic force applied to said magnetically responsive float by other means. By way of example, the relative position of the magnetic means can be changed, e.g. brought closer to the stop element to thereby increase the magnetic force. The position at which it serves to move the float element away from the stop element can then be related to the fluid flow rate through the conduit.

Alterntively, but less desired, one could increase the number of magnetic elements brough into position until such point as the requisite magnetic force was reached, the increase in number being related to fluid flow.

Of course, the resultant reading of fluid flow rate given by the aforesaid flow measuring system can be interrelated with a flow control system for varying fluid flow responsive to the reading thus obtained, and/or alternatively serve to actuate a warning system to indicate necessary changes to conditions.

The flow control system of the present invention is useful both for measuring gases and liquids. Some typical uses for such device include the following: measurement of gas supplied to pressured telephone lines or electrical cables, measurements and control of gases in analytical units, measurement of low flow rates of liquids such as in intravenous feeding systems, measurement of flows to instruments such as smoke or explosive gas or radiation or pollution detectors, and metering of fluids in blending of food or cosmetics production. The present system is particularly advantageous in situations wherein a low cost, remote indication (digital if desired), wide range, accurate flow metering system, and/or possibly sterile disposable fluid contacting element is required.

In another embodiment of the present invention, the present system can be modified to serve to measure viscosity of fluids. More specifically, by shaping the magnetic float element so as to maintain laminar flow through the conduit (at least in the area between the magnet and the stop element) and maintaining fluid velocity constant, the force on the float will be represented by the following equation:

Force = $k_{constant}$ (fluid velocity) · (fluid viscosity)

With constant fluid velocity, the force required to move the float from its position against the stop element can provide a viscosity measurement, and the apparatus serve as a linear viscosity meter. Such a linear viscosity meter is of particular value in monitoring reactions, e.g., fermentation, polymerization, paint formulation, food product preparation such as ketchup, soup manufacture, etc., cosmetics manufacture, pharmaceutical processes, etc., wherein viscosity changes are an important indication of reaction conditions, and the need for changing the operating environment. Accordingly, the linear viscosity meter thereby obtained can serve to actuate changes to reaction conditions to the system being monitored when defined viscosity values are reached, e.g. temperature change, altering of feed reactants to system, mixing conditions, etc.

The present invention is distinguished from other flow control systems such as described in inventor's U.S. Pat. No. 3,662,598. The latter utilizes the cyclic movement of a float between a sensor and a magnet with the cyclic frequency of the float element being related to the fluid flow rate. In such system the transit time of the float varies with fluid velocity. In contrast, the present invention utilizes a stop element against which the float is normally in stationary position by virtue of the fluid flow forces pressing against it. The necessary increase in magnetic force, e.g. current to an electromagnet, required to overcome the force of fluid flow to move said float element away from its normal stationary position, is related to fluid flow and utilized to measure and control same, or used to determine viscosity.

The various aspects of the present invention will be made more clearly apparent by reference to the following drawings and accompanying description.

DRAWINGS

Figure 4:
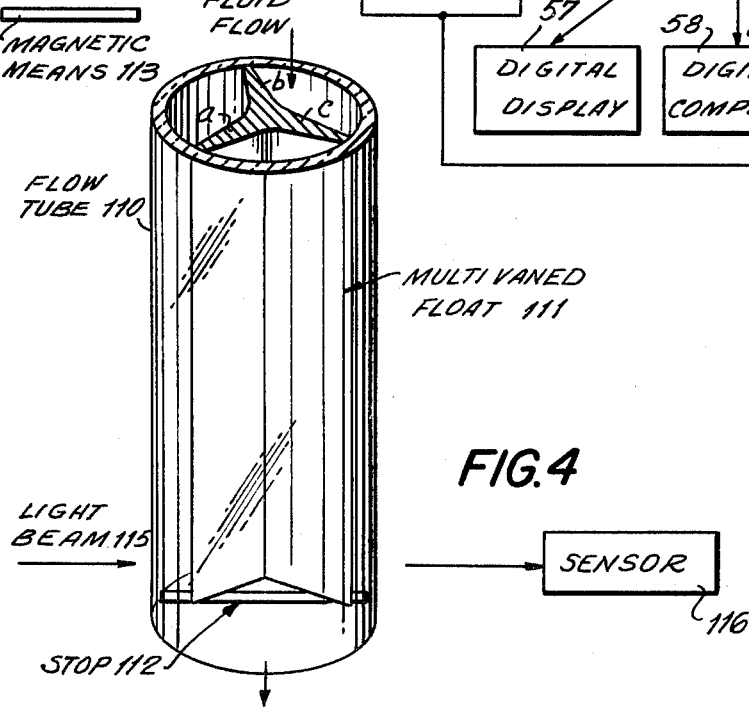

FIG. 4 illustates a float shaped to produce laminar flow.

Figure 1:
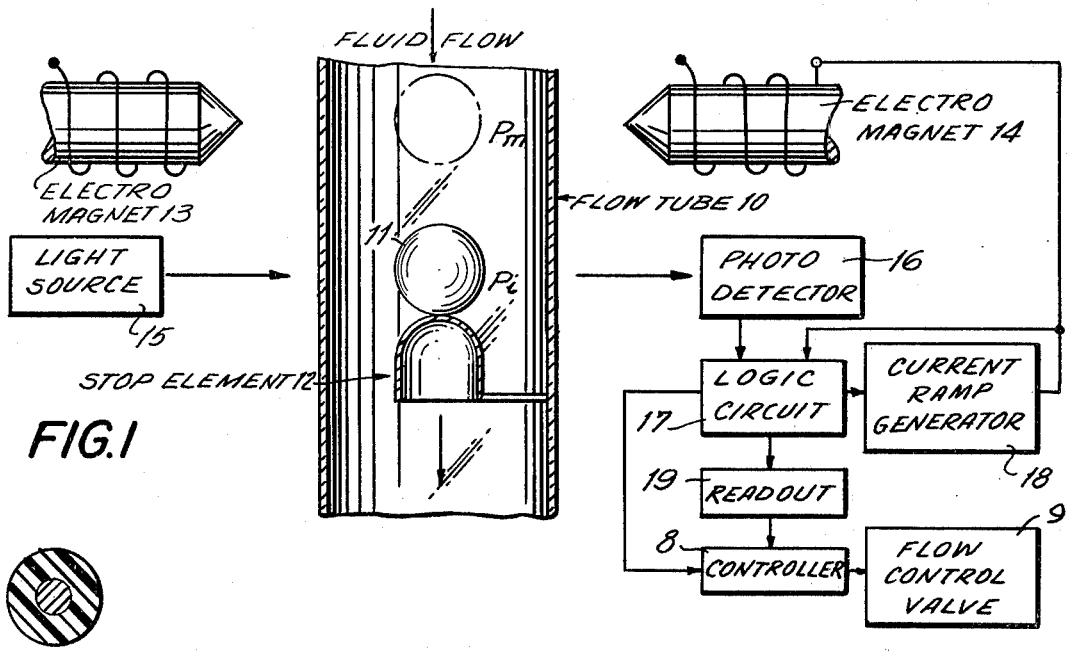
FIG. 1 illustrates a preferred flow control system employing the present invention.

With reference to FIG. 1 shown herein is a simplified system illustrating the present invention. Fluid is flowing the direction shown by the arrows through a conduit. The portion of the conduit in the area of fluid flow measurement is shown in the drawing as flow tube 10. In a typical case this can be a length of transparent tubing, e.g. transparent plastic or glass connected in a normal conduit path. Transparent tubing is normally preferred both to afford an opportunity to use a light source detector and/or afford an opportunity to visually observe the operation of the flow measurement system.

Positioned in flow tube 10 is stop element 12. Stop element 12 can be a tubular appendage, button, screen, rod or wire, normally positioned in a central portion of the flow tube so as to halt the normal flow or motion of the float element 11 and maintain it in the position shown as $P_1$. The stopping element should not be of such a size as to impede the flow of fluid past it and should be shaped to prevent significant eddy flow currents or the like which might affect the accuracy of the system. In the embodiment shown, flow tube 10 is a plastic conduit of 2 mm diameter, and stopping element 12 is a tubular element of 0.2 mm diameter made of stainless steel. It is held in position by being an integral part of the tube or fixed to its walls. Float 11, which in this embodiment takes the form of a ball, would have a diameter of about 1.8 mm. It fits more or less loosely in the tube 10 and yet is held back from flow by stopping element 12. In the specific embodiment illustrated, the float is a ball of magnetic stainless steel.

Positioned upstream of stopping element 12 are a pair of electromagnet poles 13 and 14. Normally the magnets are in fairly close position both to the flow tube 10 as well as the resting position $P_i$ of the float element since the magnetic force ultimately will have to move float element 11 away from its rest position against the force of fluid flow to position $P_m$. In the embodiment shown the magnets are about 5 mm away from the top of stopping element 12, and within 0.5 mm of the outer wall of the flow tube 10.

In a preferred embodiment, the detector for indicating the movement of the float element 11 away from its rest position takes the form of a light source 15 and detector 16 which operate are an optical detector system. A light beam shown by the arrow emitted by source 15 is blocked by opaque stainless steel ball 11 when the latter is in its rest position P. When the unit is to be used to measure fluid flow, current is increased to the electromagnets 13 and 14 by current ramp generator 18. The measurement cycle begins as the logic circuit 17 triggers the current ramp generator and the current to the electromagnet begins to slowly increases monotonically and perhaps, but not necessarily, linearly. The logic circuit 17 itself can be actuated by the operator or a timer moving a button or switch to initiate the operation of the flow measuring system. As the current from generator 18 increases the magnetic force exerted by magnets 13 and 14 on the ball also increase. The increase in magnetic force eventually overcomes the flow and perhaps gravitational forces keeping float element 11 against stop 12. When this point is reached the float element leaves the stop position and moves against the fluid flow towards the poles of the electromagnet to position $P_m$.

In the embodiment illustrated, at this point, i.e., the instant the float leaves the stop, the light beam is no longer blocked by float 11, and the light detector 16 is thereby activated. This event in turn is detected by the logic circuitry and the magnet current or voltage given off by generator 18 necessary to reach this point is sampled. The current needed to pull float 11 from its stop position, i.e. to initiate the motion of the float, is related to the pressure drop across the float and thus to the fluid flow rate, and serves as a measurement of the latter.

Typically one or more calibration curves would come with the unit (as is typical with flow meter devices), wherein the current was related to fluid flow rate for liquids within a given viscosity and density range; or alternatively the user would previously have calibrated the unit himself.

Logic circuit 17 is shown schematically. Typically, it will be actuated by the photodetector when the ball leaves the stop element. It will cause a signal proportional to the magnet current to be sent to the readout device 19 for indicating fluid flow.

The logic circuit will then normally cause the magnet current to be reset to zero for a time sufficient for the float to return to the stop element. The unit is then ready for another measurement.

Typically, when using the present system to control fluid flow, means for controlling fluid flow, such as a conventional mechanical or electromechanical valve is actuated by the measure of fluid flow thus obtained. When the flow exceeds a certain value, the valve is caused to be further closed, and when flow rate is below desired levels, the valve is actuated to further open it. Actuation can be effected by the signal given off by logic circuit 17, either directly or through readout device 19 which supplies a signal to controller 8 which then actuates flow control valve 9.

Figure 2:
FIG. 2 depicts a typical float element in the form of a plastic, ceramic, or glass ball having an iron core.

FIG. 2 illustrates an alternative form of float 11 in the form of a plastic or glass sphere 20 having a magnetically responsive core 21 of soft iron, metal filings or the like.

Figure 3:
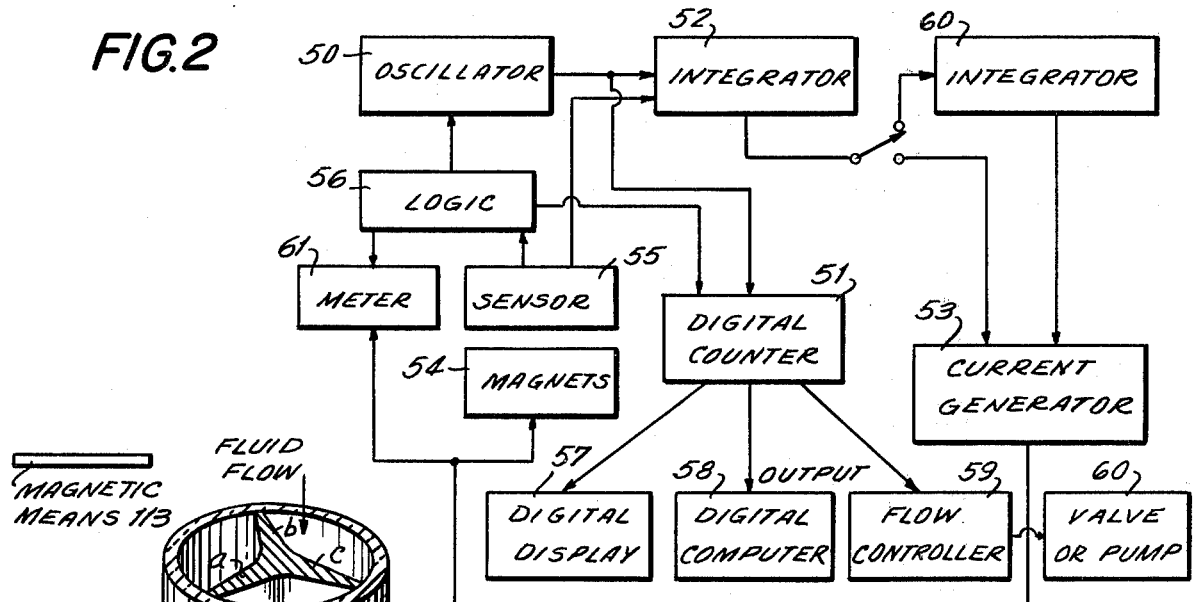
FIG. 3 is a logic diagram of a preferred operating method for flow measurement and control.

In another preferred embodiment, as illustrated in FIG. 3, the logic circuit may operate as follows to determined fluid flow rate:

At the beginning of a flow measurement, an oscillator 50 which produces a train of square wave is switched on and the output is sent to a digital counter 51 and to an integrator 52. The output of the integrator, which rises stepwise from zero in a linear fashion, is used to control by means of a current generator 53 the current to the electromagnets 54, which current also rises in a linear stepwise fashion.

When the magnet current has increased to such a level that the float or ball is pulled, against the flow forces, away from the stop element, the light beam passes through the flow tube and is detected by the photo sensor 55. At this point the oscillator 50 is turned off by the logic element 56 and the counts accumulated in the digital counter 51 are directly proportional to the magnet current needed to move the ball from the stop, and thus directly related to the fluid flow rate. Alternatively, under the control of logic element 56, the magnet current can be displayed on the meter 61.

Thus a very simple, low-cost, reliable digital output is achieved, so that the meter can be easily alternatively coupled to one or more of digital display 57, a digital computer 58, or to a flow controller 59, the latter serving to actuate a valve or pump unit 60 to vary fluid flow in response to the meter reading.

When the output of the meter has been acquired by the desired output devices, the integrator and thus the magnet current is reset to zero for a period long enough for the float or ball to return to the stop element, and the counter 51 is reset to zero (or possibly to a negative number to compensate for the effect of gravitational forces if the flow tube is mounted vertically). The meter is then ready to make another measurement of fluid flow rate.

In a modification of the above embodiment, the output of the first integrator 52 is integrated again, and the output of the second integrator 60 is used to control the magnet current. The magnet current will then be proportional to the square of the number of pulses emitted by the oscillator 50. If the flow forces are proportional to the square of the fluid velocity due to the presence of turbulent flow, the output of the counter will vary linearly with the flow rate, which in some applications will be most advantageous to permit the direct reading of flow rate.

FIG. 4 illustrates an alternative embodiment of the present invention wherein its basic principle is utilized to indicate fluid viscosity, and in particular the present element serves as a linear viscosity meter.

The elements of FIG. 3 are labeled similarly to FIG. 1. Conduit or flow tube 110 contains float element 112. In the embodiment shown stop element 112 is in the form of a flat grid or the like.

Means not shown are provided for maintaining a constant flow of fluid through conduit 110 in the direction shown by the arrow. Typically, such constant fluid flow can be maintained by a gear pump, piston pump (with constant velocity piston), or the like.

The float element 111 is especially shaped to ensure that fluid flow is laminar in the area in which the float moves. Typically, this may be done by using an elongated float element having multi-vanes a, b, and c, as shown in the drawing, although the invention contemplates any float element shaped to provided such laminar fluid flow conditions, such as a cylindrical float with a narrow clearance to the walls of the conduit.

The embodiment shown as a multi-vaned magnetic float can be made of stainless steel or be plated iron. Alternatively, a magnetic section can be connected to a non-magnetic vaned section upstream or downstream of the magnetic portion of the float.

Under conditions of laminar flow the force exerted in the float will be represented by the equation:

Force = (constant coefficient)    (fluid velocity) (fluid viscosity)

Accordingly, with the fluid velocity being held constant, the viscosity of the fluid will be proportional to the magnetic force required to move the float element 111 from stop element 112, and the resultant magnetic force can be utilized to indicate fluid viscosity.

Accordingly, in the same manner as described relative to the measurement of flow rate, the magnetic force exerted on the float element 111 by magnetic means 113 is increased until such time as the float moves away from stop 112. This in turn is sensed by the combination of light beam 115 and sensor 116. the requisite force is ascertained as described previously relative to flow rate measurement and related to fluid viscosity. The required current or other indication of magnetic force multiplied by a calibration constant factor will provide an indication of viscosity. The calibration factor for the system would previously have been ascertained by running fluids of known viscosity through the system at constant flow rate, and solving the foregoing equation.

The above system accordingly is capable of acting as an inexpensive meter capable of providing prompt and accurate viscosity measurements.

Various modifications as to elements of the present invention will suggest themselves to those skilled in the art, and are deemed included by the system defined in the following claims.

What is claimed is:

1. Apparatus for measuring flow rates of fluids comprising a conduit, a float element having a magnetic responsive material associated therewith positioned in said conduit, a stop element positioned in said conduit which limits the motion of said float element in the downstream direction, electromagnetic means positioned in an upstream portion about said conduit before said stop element, means for gradually increasing the current to said electromagnetic mean to thus increase the magnetic force of said electromagnetic means so as to move said float element away from said stop element and against the direction of fluid flow, said means for gradually increasing current to said electromagnetic means increasing current in a gradual stepwise manner to accurately measure the magnetic force required for the float to leave the stop element, means for detecting the initial departure of the float element away from the stop, and means for relating fluid flow to the degree of current required to move said float element away from said stop element.

2. The apparatus of claim 1 wherein the means for detecting the departure of the float element is positioned in the area of said stop element, said sensor means being actuated when said float element moves away from its position against said stop element, said sensor means thereby sampling the requisite reading of said means for increasing magnetic force which caused the movement of said float element from its rest position.

3. The apparatus of claim 2 wherein the conduit in the area of said stop element is transparent.

4. The apparatus of claim 3 wherein said sensor means for detecting float departure is an optical sensor.

5. The apparatus of claim 1 wherein said float element is a sphere having sufficient magnetically responsive material therein to be responsive to magnetic force of said magnetic means.

6. The apparatus of claim 1 which further comprises control means actuated by said apparatus for indicating fluid flow rate, said control means adjusting fluid flow when it varies from a predetermined level.

7. A replaceable insert adapted to be used in the apparatus of claim 1 comprising a relatively short length of tubing which contains said float means having a magnetically responsive material associated therewith in said tube, as well as said stop element positioned in said tube against which said float means normally rests when fluid flows therethrough, said replaceable insert being adapted to be inserted into said conduit means so as to coact with said magnetic means and means for detecting the departure of said float from said stop element.

8. The replaceable insert of claim 7 which is of tapered construction.

9. Apparatus for measuring flow rates of fluids comprising a vertical conduit, a float element having a magnetic responsive material associated therewith positioned in said conduit, a stop element positioned in said conduit which limits the motion of said float element, electromagnetic means positioned above said stop element, means for gradually increasing the current to said electromagnetic means to thus increase the magnetic force of said electromagnetic means so as to move said float element away from said stop element, said means for gradually increasing current to said electromagnetic means increasing current in a gradual stepwise manner to accurately measure the magnetic force required for the float to leave the stop element, means for detecting the initial departure of the float from the stop element, and means for relating fluid flow to the degree of current required to move said float element away from said stop element.

10. Apparatus for measuring flow rates of fluids comprising a conduit, a float element having a magnetic responsive material associated therewith positioned in said conduit, a stop element positioned in said conduit which limits the motion of said float element in the downstream direction, electromagnetic means positioned in an upstream portion about said conduit before said stop element, means for gradually increasing the current to said electromagnetic means to thus increase the magnetic force of said electromagnetic means so as to move said float element away from said stop element and against the direction of fluid flow, means for detecting the initial departure of the float element away from the stop, and means for relating fluid flow to the degree of requisite increase of current to cause movement of said float element away from said stop element, said means for gradually increasing current comprising an oscillator, and an integrator, and which apparatus further contains a digital counter, said oscillator producing a wave train sent to the digital counter and integrator, said integrator controlling the current to the electromagnetic means proportional to the output of the integrator, said oscillator being turned off when said float element departs from said stop element, the accumulated counts in the digital counter being directly related to fluid flow rate.

11. The apparatus of claim 10 which further comprises a second integrator, the output of the first integrator being integrated in said second integrator and the output of said second integrator being used to control the means for increasing current to said electromagnet, so that the current is proportional to the output of the second integrator, the output of said digital counter thereby being capable of linear variation with fluid flow.

12. The apparatus of claim 10 wherein said means for gradually increasing current to said magnetic means increases in a gradual stepwise manner.

13. The apparatus of claim 10 wherein the means for detecting the departure of the float element is positioned in the area of said stop element, said sensor means being actuated when said float element moves away from its position against said stop element, said sensor means thereby sampling the requisite reading of said means for increasing magnetic force which caused the movement of said float element from its rest position.

14. The apparatus of claim 13 wherein the conduit in the area of said stop element is transparent.

15. The apparatus of claim 14 wherein said sensor means for detecting float departure is an optical sensor.

16. The apparatus of claim 10 wherein said float element is a sphere having sufficient magnetically responsive material therein to be responsive to magnetic force of said magnetic means.

17. The apparatus of claim 10 which further comprises control means actuated by said apparatus for indicating fluid flow rate, said control means adjusting fluid flow when it varies from a predetermined level.

* * * * *